(12) United States Patent
Birkner

(10) Patent No.: US 7,803,935 B2
(45) Date of Patent: Sep. 28, 2010

(54) NUCLEIC ACID ADSORPTION UNDER LOW-SALT CONDITIONS

(75) Inventor: Christian Birkner, Uffing (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 127 days.

(21) Appl. No.: 12/105,381

(22) Filed: Apr. 18, 2008

(65) Prior Publication Data

US 2009/0012285 A1    Jan. 8, 2009

(30) Foreign Application Priority Data

Apr. 20, 2007   (EP)   ................... 07008072

(51) Int. Cl.
*C07H 21/00* (2006.01)

(52) U.S. Cl. ................... 536/25.41; 536/22.1; 536/25.4

(58) Field of Classification Search .................. None
See application file for complete search history.

(56) References Cited

OTHER PUBLICATIONS

Bailly et al. Biochemistry (2005), vol. 44, pp. 1941-1952.*
Onda et al. JACS (1996), vol. 118, pp. 8524-8530.*

* cited by examiner

*Primary Examiner*—Patrick T Lewis
(74) *Attorney, Agent, or Firm*—Marilyn L. Amick; Roche Diagnostics Operations, Inc.

(57) ABSTRACT

Biscationic organic compounds are disclosed which promote adsorption of nucleic acids from an aqueous solution to a solid phase such as silica. Adsorption takes place under low salt conditions. Further disclosed are methods and kits suitable for nucleic acid isolation from aqueous solutions.

7 Claims, 4 Drawing Sheets

NUCLEIC ACID ADSORPTION UNDER LOW-SALT CONDITIONS

RELATED APPLICATIONS

This application claims priority to EP 07008072.6 filed Apr. 20, 2007.

FIELD OF THE INVENTION

The present invention relates to the purification of nucleic acids.

BACKGROUND OF THE INVENTION

Numerous methods are known to art which disclose the isolation of nucleic acids from sample material. To this end, methods for sample preparation are of high importance.

Particularly useful methods achieve this purpose by way of lysing the sample material and adsorbing nucleic acids to a solid phase (e.g., a silica matrix) in the presence of a chaotropic substance. By way of separating the select phase from the remaining lysate and subsequent desorption of the nucleic acid from the solid phase, the nucleic acid can be isolated efficiently.

During the adsorption process, the chaotropic substance effects removal of water molecules from the hydrate shell of dissolved nucleic acid molecules as well as from the surface of the solid phase, e.g., a silica matrix. As a result, a direct ionic interaction between the —Si—OH groups of the silica matrix and the phosphate-diester groups of the nucleic acid backbone becomes possible (Melzak, K. A., et al., J. Coll. Interf. Sci. 181 (1996) 635-644).

In the state of the art, the chaotropic substance is applied at very high concentrations in the range between 1 M to 6 M or even higher. Additives, e.g., other elements as boron, iron, phosphor, aluminum and the like, present in the silica matrix may influence the ability of the solid phase to bind to nucleic acids.

The described chaotropic effect is accompanied by an increase of the entropy. Thus, the equilibrium is shifted to the binding of the nucleic acid to the surface of the solid phase. As a prerequisite, however, the surface of the solid phase has to be in a neutral state. Especially for the surface of a silica material, the preferred pH range for adsorbing the nucleic acid is between pH 4 and pH 6.

The chaotropic effect can be enhanced by the addition of other dehydrating substances. For example, addition of an organic solvent, e.g., an alcohol, results in an improved adsorption of nucleic acids to glass surfaces. Alcohol concentrations usually are in the range between 30% and 60% [v/v]. In addition, alcohol appears to shift the selectivity towards binding nucleic acids, at the expense of other organic compounds.

Further, detergents are added at high concentrations (e.g., TRITON X-100, 20% [v/v]) to enhance lysis of the sample material. At the same time, detergents can positively influence the process of adsorption of nucleic acids to the solid phase.

A further advantage of chaotropic substances at high concentrations is an inhibition of nucleases which may be present in the lysate. This particular effect can be enhanced by adding reducing compounds such as dithiothreitol (DTT).

The state of the art has certain disadvantages. To achieve the desired adsorption of nucleic acids onto the solid phase compositions have to be formed which are very complex and which contain reagents—particularly one or more salts—at very high concentrations in order to achieve sufficient binding and selectivity. Depending on the complexity of the sample material before treatment, undesired constituents and particularly proteins have to be pretreated specifically. To this end, sample material is frequently digested with a proteinase, e.g., proteinase K. However, high concentrations of chaotropic substances inhibit proteinase activity. Although this shortcoming can be overcome by applying high quantities of proteolytic enzyme, this approach increases the costs of sample preparation since the protease needs to be of very high quality, that is to say, it must be free of nucleases. A further disadvantage is the frequent need of alcohol which is flammable and thus requiring safety precautions. Apart from safety concerns in the laboratory with regards to alcohol, this organic compound poses additional problems when being pipetted. The vapor pressure of alcohols such as ethanol or isopropanol is a particular technical problem with regards to automated handling of liquids.

It was therefore an object of the invention to provide alternative compositions for adsorbing a nucleic acid from a liquid phase to a solid phase. It was a particular object of the invention to provide compositions with organic additives which overcome at least some of the disadvantages of alcohols. A further particular object of the invention was to provide compositions which allow the adsorption of the nucleic acid to the solid phase in the presence of lower salt concentrations than in the state of the art.

SUMMARY OF THE INVENTION

A first aspect of the invention is the use of a biscationic organic compound for binding a nucleic acid to a solid phase. According to the invention, the biscationic compound is selected from the group consisting of a bis-benzimidazolium cation, a bis-imidazolium cation, and a bis-guanidinium cation. Another aspect of the invention is an aqueous composition for adsorbing a nucleic acid to a solid phase, wherein the composition is a solution of compounds comprising a buffer salt, a biscationic organic compound, and a nucleic acid, whereby the salt concentration in the composition excluding the biscationic compound and its one or more counter ions is between 5 mM and 300 mM. Another aspect of the invention is a method for purifying a nucleic acid comprising the steps of (a) providing the following components: (i) a solid phase capable of reversibly binding nucleic acids; (ii) an aqueous buffered solution containing the nucleic acid and biscationic organic compound; (b) contacting the provided components under conditions suitable for adsorbing the nucleic acid to the solid phase; (c) separating the solid phase with the adsorbed nucleic acid from the solution; (d) eluting the nucleic acid from the solid phase; thereby purifying the nucleic acid. Yet another aspect is a kit of parts for isolating a nucleic acid, comprising a solid phase capable of reversibly binding nucleic acids and vial containing a buffered solution of a biscationic compound. A further aspect includes the kit according to the invention, characterized in that the solid phase is a silica fleece or magnetic particles coated with silica.

DETAILED DESCRIPTION OF THE INVENTION

Figure 1:
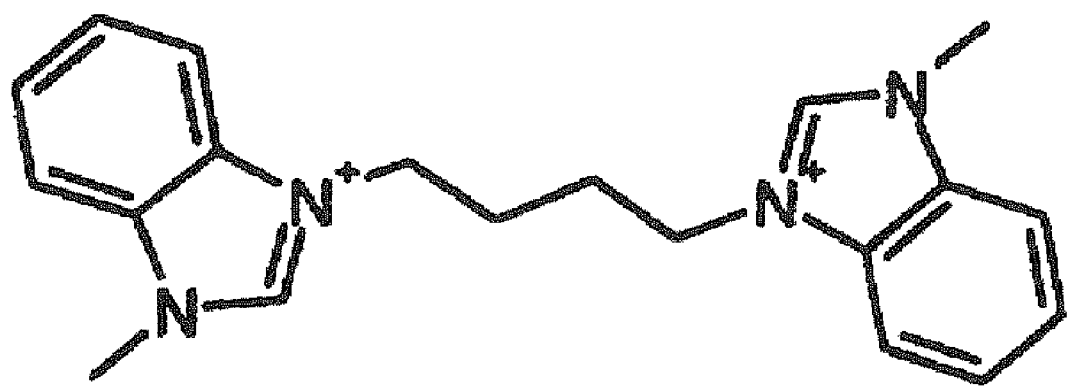
FIG. 1: MBITS (1H-benzimidazolium, 1,1'-(1,4-butanediyl)bis[3-methyl]) cation.
Figure 2:
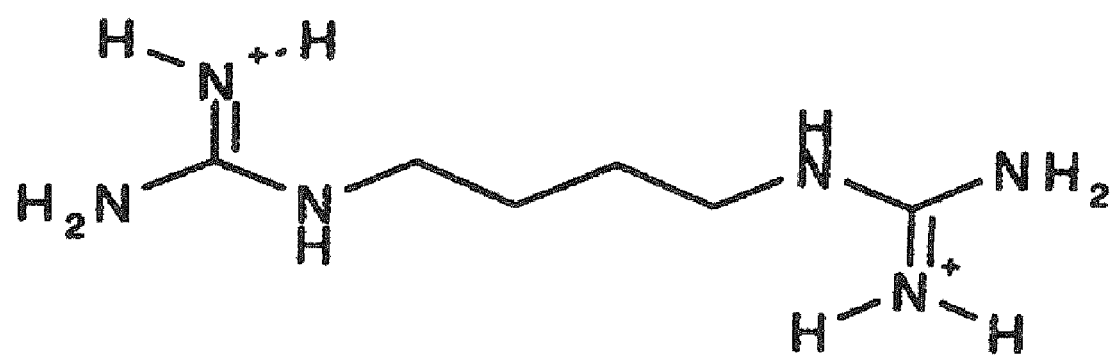
FIG. 2: BGDS (guanidine, N,N'''-1,4-butanediyl)cation.
Figure 3:
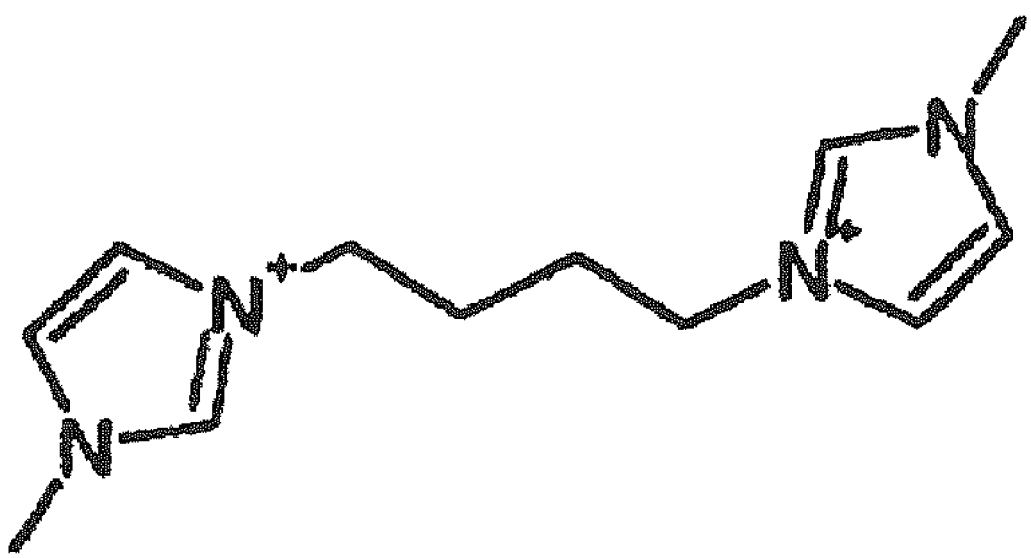
FIG. 3: MITS (1H-imidazolium, 1,1'-(1,4-butanediyl)bis [3-methyl-]) cation.
Figure 4:
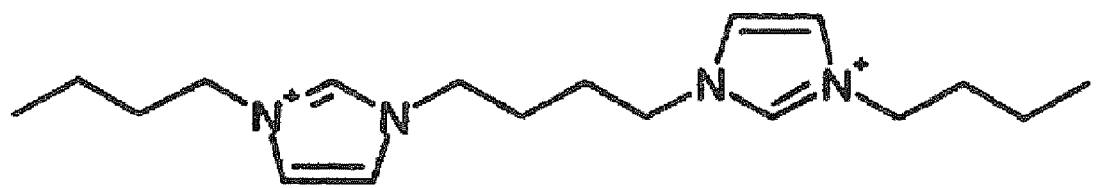
FIG. 4: BITS (1H-imidazolium, 1,1'-(1,4-butanediyl)bis [3-butyl-]) cation.

The present invention provides new compositions and methods for the purification of nucleic acids. Certain terms are used with particular meaning or are defined for the first time in this description of the present invention. For the purposes of the present invention, the terms used are defined by their art-accepted definitions, when such exist, except that when those definitions conflict or partially conflict with the definitions set forth below. In the event of a conflict in definition, the meaning of a terms is first defined by any of the definitions set forth below.

The term "comprising" is used in the description of the invention and in the claims to mean "including, but not necessarily limited to".

The articles "a" and "an" are used herein to refer to one or to more than one (i.e., to at least one) of the grammatical object of the article. By way of example, "a compound" means one compound or more than one compound.

When designating a range of numerical values such as a concentration range, the range is indicated by the word "between", followed by a first value n1 and a second value n2. The lower boundary of the designated range is understood as being the value equal to or higher than the first value. The higher boundary of the designated range is understood as being the value equal to or lower than the second value". Thus, a value x the designated range is given by $n1 \leq x \leq n2$.

Further, it is understood that the term "about" in combination with a numerical value n indicates a value x in the interval given by the numerical value ±5% of the value, i.e., $n-0.05*n \leq x \leq n+0.05*n$. In case the term "about" in combination with a numerical value n describes a preferred embodiment of the invention, the value of n is most preferred, if not indicated otherwise.

The term "solid phase" to which a nucleic acid is adsorbed is understood as being a substrate which is insoluble in the compositions according to the invention. A preferred solid phase is a substrate with a surface capable of interacting with the phosphate groups of the backbone of nucleic acids. The solid phase may be in the form of porous or non-porous particles, powdered particles, or fibers. A solid phase consisting of fleece material which comprises a plurality of non-woven fibers is also encompassed. Preferred solid phases consist of glass. Preferred solid phases are porous or non-porous mineral substrates such as silica, quartz, celites, or other materials with oxidic surfaces (including, e.g., zirconium oxide, aluminum oxide, and other metal oxides) or mixtures thereof. Also, the term "solid phase" encompasses magnetically attractable particles coated with silica, glass, quartz, or celites. Further, it is understood that a substrate in the form of "powder" or "powdered" material refers to finely divided material which, when dispersed in a liquid composition according to the invention, produces a suspension. The term "powder" or "powdered" material is intended to include tablets in which the powdered material has been aggregated but still yields a suspension when combined with a liquid phase.

The term "silica" as used within this application denotes materials which are mainly build up of silicon and oxygen. These materials comprise silica, silicon dioxide, silica gel, fumed silica gel, diatomaceous earth, celite, talc, quartz, glass, glass particles including all different shapes of these materials. Glass particles, for example, may comprise particles of crystalline silica, soda-lime glasses, borosilicate glasses, and fibrous, non-woven glass.

The term "magnetic particle" denotes a particle with paramagnetic or superparamagnetic properties. That is to say, the particle is magnetically displaceable but does not retain any magnetization in the absence of an externally applied magnetic field.

The term "sample" (or "sample material") as used herein refers to a complex sample, more preferred a biological sample. A complex sample may contain a plurality of organic and inorganic compounds which are desired to be separated from the nucleic acid. The term "sample" also encompasses an aqueous solution containing nucleic acids derived from other origins, e.g., from chemical or enzymatic reaction mixtures, or from a previous purification of biological sample material. The term biological sample, from which nucleic acids are purified, encompasses samples comprising viruses or bacterial cells, as well as isolated cells from multicellular organisms such as human and animal cells as well as tissues and cell cultures. Particularly, the sample can contain leukocytes and other immunologically active cells, chemical compounds with a low and/or a high molecular weight such as haptens, antigens, antibodies and nucleic acids. The sample can be whole blood, blood serum, blood plasma, cerebral fluid, sputum, stool, biopsy specimens, bone marrow, oral rinses, tissues, urine, or mixtures thereof. The present invention also encompasses biological samples such as a fluid from the human or animal body; preferably the biological sample is blood, blood plasma, blood serum or urine. The blood plasma is preferably EDTA, heparin or citrate blood plasma. In an embodiment of the invention, the biological sample comprises bacterial cells, eukaryotic cells, viruses, or mixtures thereof. A biological sample as exemplified above, preferably in a processed form such as a lysate, can be part of the composition from which the (target) nucleic acid is adsorbed to the substrate. Also encompassed by the term "biological sample" are cells from plants and fungi as well as single cell organisms.

A preferred sample according to the invention is a lysate. A "lysate" or a "lysed sample" can be obtained from a complex sample and/or biological sample material comprising tissue, cells, bacteria, or viruses whereby the structural integrity of the material is disrupted. To release the contents of cells, tissue, or more generally, from the particles which make up a biological sample, the material may be treated with enzymes or with chemicals to dissolve, degrade, or denature the cellular walls and cellular membranes of such organisms. This process is encompassed by the term "lysis". It is common to use chaotropic agents such as a guanidinium salt and/or anionic, cationic, zwitterionic or non-ionic detergent when nucleic acids are set free in the lysis process. It is also an advantage to use proteases which rapidly degrade enzymes with nucleolytic activity and other unwanted proteins. In case there remains particulate, i.e., undissolved matter of the sample material following the lysis process, the particulate matter is usually separated from the lysate to result in a cleared lysate. This can be done, e.g., by way of filtering or centrifugation. In such a case the cleared lysate is processed further, e.g., by a method according to the invention. Thus, the term "lysed sample" encompasses a cleared lysate.

A "chaotropic agent" according to the present invention is any chemical substance which disturbs the ordered structure of liquid water. A chaotropic agent also facilitates unfolding, extension, and dissociation of proteins (Dandliker, W. B., and de Saussure, V. A.: The Chemistry of Biosurfaces, Hair, M. L., ed., Marcel Dekker, Inc. New York (1971) p. 18). Preferred chaotropic salts are sodium iodide, sodium perchlorate, guanidinium thiocyanate, guanidinium isothiocyanate, or guanidinium hydrochloride. Another preferred chaotropic agent is urea.

The terms "aqueous", "aqueous" phase, and "aqueous" solution describe a liquid phase of which the solvent portion comprises water. However, other solvents such as a water-miscible organic solvent can be present in the solvent portion, too. In view of the presence of other solvents, a solution is considered "aqueous" when between 30% and 100%, measured as volume by volume [v/v], of the solvent portion is water.

The term "nucleic acid" as used within this application denotes DNA and RNA polynucleotides of natural and synthetic origin. This includes modified nucleotides as, e.g., dideoxyribonucleotides, nucleobases with modified sugar residues, and nucleobases with modified base moieties (see e.g., Scheit, K. H., Nucleotide Analogs, John Wiley and Sons, N.Y. (1980); Uhlmann, E., and Peyman, A., Chem. Rev. 90 (1990) 543-584). In particular genomic DNA, complementary DNA (cDNA), messenger RNA (mRNA), transfer RNA (tRNA), ribosomal RNA (rRNA) and micro RNA (miRNA) is included.

The term "adsorption"/"adsorbing" generally means adhere or attach molecules or ions (the "solute") to outer surfaces or interfaces so as to increase the concentration of a solute in the vicinity of a solid surface, over that in the bulk of the solution due to the attractive interaction between the solid immersed into the solution and the solute. The binding to the surface is usually weak and reversible. It is a surface process such that the accumulating molecules do not actually penetrate the substance on which they are formed. The term is not to be confused with absorption which means the filling of pores in a solid.

The isolation and purification of nucleic acids is often linked with the use of chaotropic agents like guanidinium salts in high concentrations for adsorbing the nucleic acids to solid phases such as silica matrices (Vogelstein, B., and Gillespie, D., Proc. Natl. Acad. Sci. USA 76 (1979) 615-619; Marko, M., A., et al., Anal. Biochem. 121 (1982) 382-387).

Examples for chaotropic salts are guanidinium salts such as guanidinium thiocyanate, guanidinium isothiocyanate, or guanidinium hydrochloride but also sodium iodide, sodium perchlorate. Other compounds known to the skilled artisan are also possible. A chaotropic substance effects removal of water molecules from the hydrate shell of dissolved nucleic acid molecules as well as from the surface of the solid phase, e.g., a silica matrix. As a result, a direct ionic interaction between the —Si—OH groups of the silica matrix and the phosphate-diester groups of the nucleic acid backbone becomes possible in this particular case (Melzak, K. A., et al., J. Coll. Interf. Sci. 181 (1996) 635-644).

The described chaotropic effect is accompanied by an increase of the entropy. Thus, the equilibrium is shifted to the binding of the nucleic acid to the surface of the solid phase. As a prerequisite, the surface of the solid phase has to be in a neutral state. Especially for the surface of a silica material, the preferred pH range for adsorbing the nucleic acid is between pH 4 and pH 6. Additives, e.g., other elements as boron, iron, phosphor, aluminum, and the like, present in the silica matrix may shift the appropriate conditions. The chaotropic effect can be enhanced by the addition of other dehydrating substances. For example, addition of an organic solvent, e.g., an alcohol, results in an improved adsorption of nucleic acids to glass surfaces.

The inventors surprisingly found that certain ionic liquids have an effect which is similar to the effect of chaotropic agents. The inventors could show that a biscationic organic compound can efficiently promote the adsorption of nucleic acids from an aqueous solution to a solid phase.

A first aspect of the current invention therefore is the use of a biscationic organic compound for binding a nucleic acid to a solid phase. Preferably, the biscationic compound is selected from the group consisting of a bis-benzimidazolium cation, a bis-imidazolium cation, and a bis-guanidinium cation. Even more preferred, the biscationic compound is selected from the group consisting of MBITS, BGDS, MITS, and BITS.

Preferably, the biscationic compounds according to the invention are used as ditosylsulfonates. However other counter ions are possible.

A biscationic organic compound according to the invention is capable of promoting the adsorption of a nucleic acid to a solid phase, preferably a solid phase with a silica surface, and preferably under acidic conditions without the further need of a chaotropic substance.

Even more surprising, adsorption in the presence of a biscationic organic compound takes place even at salt concentrations below 500 mM.

When referring to the salt concentration in the adsorption solution according to the invention, e.g., a low salt concentration, it is understood that the concentration of the biscationic organic compound including its one or more counter ions is disregarded. Thus, the salt concentration comprises all other salts such as inorganic salts (e.g., salts comprised in a sample such as a biological sample) and buffer salts.

Preferably, the salt concentration in the adsorption solution is in the range of between about 10 mM and about 250 mM. Even more preferred, the salt concentration is between about 20 mM and 150 mM. Even more preferred, the salt concentration is between about 25 mM and 100 mM.

A further aspect of the present invention is therefore an aqueous composition for adsorbing a nucleic acid to a solid phase, characterized in that the composition is a solution of compounds comprising a buffer salt, a biscationic organic compound, and a nucleic acid, whereby the salt concentration in the composition excluding the biscationic compound and its one or more counter ions is between 5 mM and 300 mM. More preferred, the salt concentration is between 10 mM and 250 mM, even more preferred between 20 mM and 200 mM.

An aqueous composition according to the invention is also referred to as an "adsorption solution".

Preferably, the pH of the composition according to the invention is adjusted to a value between about pH 4.0 and about 7.5. More preferred, the pH is between about 4.0 and 6.5, and also very much preferred between 5.5 and 6.5. It is obvious for the skilled person to produce suitable aqueous buffered solutions. Buffer systems which are suitable for molecular biology purposes may be found, e.g., in Sambrook, J., et al, Molecular Cloning, A Laboratory Manual, 3rd edition, CSHL Press (2001) Cold Spring Harbor, N.Y. Preferred buffer substances are tris-(hydroxymethyl)-aminomethane (TRIS), 2-morpholinoethanesulfonic acid (MES) phosphate, N-(2-hydroxyethyl)piperazine-N-(2-ethanesulfonic acid) (HEPES), acetate, salts thereof, and other suitable substances.

A further aspect of the present invention is a method for purifying a nucleic acid, characterized in that the method comprises the steps of (a) providing the following components: (i) a solid phase capable of reversibly binding nucleic acids; (ii) an aqueous buffered solution containing the nucleic acid and biscationic organic compound; (b) contacting the provided components under conditions suitable for adsorbing the nucleic acid to the solid phase; (c) separating the solid phase with the adsorbed nucleic acid from the solution; (d) eluting the nucleic acid from the solid phase; thereby purifying the nucleic acid. In step (c) the nucleic acid is separated from the biscationic compound. Preferably, following step (c) before step (d) is executed, the solid phase with the bound nucleic acid is subjected to a washing step, whereby the washing solution contains an alcohol.

Generally, the preferred solid phase to which the nucleic acid is adsorbed using the compositions and methods according to the invention comprises a porous or non-porous solid substrate. Very much preferred is a silica substrate. More preferred, the silica substrate is selected from the group consisting of silica gel, glass fibers, quartz fibers, and celites. Also preferred, the solid phase comprises a porous or non-porous mineral substrate selected from the group consisting of metal oxides, and/or metal mixed oxides, alumina, titania, zirconia, and materials predominantly consisting of glass.

It is also preferred that the solid phase has a particle size of 0.1 μm to 100 μm. It is also preferred that porous solid phase materials, when employed, have a pore size of from 2 to 1,000 nm. More preferred, porous or non-porous solid phase materials, especially celites, are in the form of loose packings. Even more preferred, the solid phase consists of filter sheets in the form of glass, quartz, or ceramic filter sheets, and/or a membrane containing silica gel and/or particles or fibers of mineral substrates and fabrics of quartz or glass wool, that is to say fibrous, non-woven glass.

It is also preferred that the solid phase comprises magnetically attractable particles. More preferred, the magnetically attractable particles are coated with a mineral substrate selected from the group consisting of silica, glass, quartz, and celites. Even more preferred, the substrate comprises magnetically attractable particles coated with glass. The magnetic glass particles used in the present invention may be provided in different formulations. It is possible to provide them in the form of a tablet, as a powder, or as a suspension. Very much preferred, the magnetic glass particles are suspended in a liquid composition according to the invention. Preferably, these suspensions contain between 5 to 100 mg/ml magnetic glass particles (MGPs). Also preferred, the silica-containing material is suspended in aqueous buffered solutions which may optionally contain an ionic liquid according to the invention.

The nucleic acid can be comprised in sample material. Hence, the sample material can be part of the composition of step (a) (ii). The sample material is preferably homogenized in the composition before step (b) is performed. The sample material may comprise biological material. Also in this case, a homogenization step is preferably performed before step (b). If necessary, after homogenization residual particulate matter such as cell debris is separated from the remaining homogenized sample material by centrifugation, and the supernatant is further processed by executing step (b). Alternative separation techniques are known, apart from centrifugation, including filtration.

The purification effect of the method according to the invention results from the behavior of DNA or RNA to bind to material of the solid phase under these conditions, i.e., in the presence of the compositions according to the invention. To bring the sample in contact with the substrate, i.e., the material with an affinity to nucleic acids, the sample is mixed with the material and incubated for a period of time sufficient for the binding to occur. Experts are usually familiar with the duration of the incubation step from procedures for performing comparable treatment of solid phases in the presence of, e.g., an alcohol and a chaotropic salt as described in the state of the art. This step can be optimized by determining the quantity of immobilized nucleic acid on the surface of the solid phase at different points in time. Incubation times of between 10 seconds and 30 minutes can be appropriate for nucleic acids. After incubation, the adsorbed target component is separated from the liquid phase. This may be achieved in general by gravity.

In the convenient case of nucleic acids bound to magnetic glass particles, the separation step is performed by way of applying a magnetic field to the magnetic particles with the adsorbed nucleic acid material. For instance, the magnetic particles can be pulled to the wall of the vessel in which incubation was performed. The liquid containing the sample contents that are not bound to the magnetic particles can then be removed. The removal procedure used depends on the type of vessel in which incubation was performed. Suitable steps include removing the liquid via pipetting or aspiration.

Another preferred way is the use of so-called "spin columns" or "spin filter columns" which are commercially available such as HIGH PURE columns from Roche Diagnostics GmbH Mannheim, Germany. Spin filter column tubes usually contain a fleece of non-woven glass fibers located at the bottom of the column and covering the opening at the bottom. The adsorption solution containing the nucleic acid is transferred to the column and passed through the fleece by applying force. The term "force" includes gravitational force and, preferred, centrifugal force. Very much preferred is the "spin column" procedure wherein the adsorption solution is passed through the filter due to force being applied by way of centrifugation. Other ways to pass the adsorption solution through the fleece include the application of pressure or suction.

The solid phase with the adsorbed nucleic acid may then be washed at least once with a wash solution. The washing step or steps is optional. A wash solution is used that does not cause the target component to be released from the material surface but that washes away the undesired contaminants as thoroughly as possible. This wash step preferably takes place by incubating the material with the bound target nucleic acid (s) with the wash solution. The material is preferably resuspended during this step. Also preferred, in case the material is a glass fleece or a packing in a column, the washing step takes place by rinsing the column with the washing solution. Preferably, the washing solution is passed through the column by applying pressure, suction, centrifugal force or gravitational force. Suitable wash solutions are known to the skilled person and may contain a salt, a chaotropic substance, and/or an organic solvent such as an alcohol. The contaminated wash solution is preferably removed just as in the step described above for adsorbing the nucleic acid to the solid phase. After the last washing step, the separated material of the solid phase with the adsorbed nucleic acids can be dried briefly in a vacuum or the fluid can be allowed to evaporate. A pretreatment step using acetone may also be performed.

Afterwards, the conditions are changed to release the nucleic acid from the solid phase. This step is also referred to as "eluting" the nucleic acid. The solid phase with the immobilized biological material is contacted with an aqueous solution with no or only a low amount of chaotropic agent and/or organic solvent and/or liquid ion. Alternatively, the suspension can be diluted with a solution with no or only a low amount of chaotropic agent and/or organic solvent and/or liquid ion. Buffers of this nature are known to the skilled person, e.g., from DE 37 24 442 and Jakobi, R., et al., Anal. Biochem. 175 (1988) 196-201. The elution buffers with a low salt content are in particular buffers with a content of less than 0.2 mol/l. Preferably, the elution buffer contains the substance tris for buffering purposes. Also preferred, the elution buffer is demineralized water. The solution containing the purified nucleic acid can now be used for other reactions. Optionally, the nucleic acid(s) can be precipitated from the solution using, e.g., ethanol or isopropanol. The precipitate can also be subjected to further washing steps. Methods of this kind are well known to the skilled artisan and are described in detail in Sambrook, J., et al., Molecular Cloning, A Laboratory Manual, 3rd edition, CSHL Press (2001) Cold Spring Harbor, N.Y.

The invention also contemplates kits. Such kits known to the art comprise plasticware useful in the sample preparation procedure. Examples therefor are microwell plates in the 96- or 384-well format or just ordinary reaction tubes manufactured, e.g., by Eppendorf, Hamburg, Germany. The kits of the invention also comprise some or all other reagents for carrying out the methods according to the invention. Therefore, a kit can additionally contain a solid phase, i.e., a material with an affinity to nucleic acids. Preferably the solid phase comprises a material with a silica surface. Very much preferred, the solid phase comprises glass or quartz fibers. Also very much preferred, the solid phase is a composition comprising magnetic glass particles, i.e., magnetically attractable particles coated with glass. The kit can further or additionally comprise a lysis buffer containing a biscationic organic compound according to the invention, a detergent, or mixtures thereof. These components of the kit according to the invention may be provided separately in tubes or storage containers. Depending on the nature of the components, these may be even provided in a single tube or storage container. The kit may further or additionally comprise a washing solution which is suitable for the washing step of the solid phase when DNA or RNA or both are bound thereto. This washing solution may contain a chaotropic agent in a buffered solution or solutions with an acidic pH. Additionally, the washing solution may contain a C1-C5 alcohol. Preferably, the alcohol is ethanol or isopropanol.

Often the washing solution or other solutions are provided as stock solutions which have to be diluted before use. The kit may further or additionally comprise a desorption solution, i.e., an elution buffer, that is to say, a solution for desorbing the nucleic acid from the solid phase. A preferred desorption solution can be a buffer (e.g., 10 mM Tris, 1 mM EDTA, pH 8.0) or pure water. Further, additional reagents or buffered solutions may be present which can be used for the purification process of a nucleic acid, i.e., DNA or RNA. Thus, another aspect of the invention is a kit for isolating nucleic acids from nucleic acid containing material, characterized in that the kit comprises a solid phase capable of reversibly binding nucleic acids and a vial containing a buffered solution of a biscationic compound. Preferably, the solid phase is a silica fleece or magnetic particles coated with silica. Very much preferred, the biscationic compound is selected from the group consisting of MBITS, BGDS, MITS, and BITS.

In more detail, the present invention comprises the following points:

1. Use of a biscationic organic compound for binding a nucleic acid to a solid phase.
2. The use according to point 1 in the absence of a guanidinium salt.
3. The use according to point 1 in the absence of one or more compounds selected from the group consisting of sodium iodide, sodium perchlorate, guanidinium thiocyanate, guanidinium isothiocyanate, guanidinium hydrochloride, and urea.
4. The use according to any of the points 1 to 3 in the absence of ethanol and isopropanol.
5. The use according to any of the points 1 to 3 in the absence of a C1-C5 aliphatic alcohol.
6. The use according to any of the points 1 to 5, characterized in that the nucleic acid is DNA or RNA.
7. The use according to any of the points 1 to 6 in the presence of one or more salts, whereby the one or more salts are present at a concentration below 500 mM.
8. The use according to any of the points 1 to 6 in the presence of one or more salts, whereby the one or more salts are present at a concentration of between 1 mM and 400 mM.
9. The use according to point 8 in the presence of one or more salts, whereby the one or more salts are present at a concentration of between 5 mM and 300 mM.
10. The use according to point 9 in the presence of one or more salts, whereby the one or more salts are present at a concentration of between 10 mM and 250 mM.
11. The use according to point 10 in the presence of one or more salts, whereby the one or more salts are present at a concentration of between 20 mM and 150 mM.
12. The use according to point 10 in the presence of one or more salts, whereby the one or more salts are present at a concentration of between 25 mM and 100 mM.
13. The use according to any of the points 1 to 12, characterized in that the biscationic compound is selected from the group consisting of a bis-benzimidazolium cation, a bis-imidazolium cation, and a bis-guanidinium cation.
14. An aqueous composition for adsorbing a nucleic acid to a solid phase, characterized in that the composition is a solution of compounds comprising
    a. a buffer salt;
    b. a biscationic organic compound;
    c. a nucleic acid;
    whereby the salt concentration in the composition excluding the biscationic compound and its one or more counter ions is between below 500 mM.
15. The aqueous composition of point 14, characterized in that the composition is a solution of compounds excluding a guanidinium salt.
16. The aqueous composition of point 14, characterized in that the composition is a solution of compounds excluding one or more compounds selected from the group consisting of sodium iodide, sodium perchlorate, guanidinium thiocyanate, guanidinium isothiocyanate, guanidinium hydrochloride, and urea.
17. The aqueous composition of point 14, characterized in that the composition is a solution of compounds excluding one or more chaotropic agents.
18. The aqueous composition according to any of the points 14 to 17, characterized in that the composition is a solution of compounds excluding ethanol and isopropanol.
19. The aqueous composition according to any of the points 14 to 17 characterized in that the composition is a solution of compounds excluding a C1-C5 aliphatic alcohol.
20. The aqueous composition according to any of the points 14 to 19, characterized in that the nucleic acid is DNA or RNA.
21. The aqueous composition according to any of the points 14 to 20, characterized in that the salt concentration in the composition excluding the biscationic compound and its one or more counter ions is between 1 mM and 400 mM.
22. The aqueous composition according to point 21, characterized in that the salt concentration in the composition excluding the biscationic compound and its one or more counter ions is between 5 mM and 300 mM.
23. The aqueous composition according to point 22, characterized in that the salt concentration in the composition excluding the biscationic compound and its one or more counter ions is between 10 mM and 250 mM.
24. The aqueous composition according to point 23, characterized in that the salt concentration in the composition excluding the biscationic compound and its one or more counter ions is between 20 mM and 150 mM.

25. The aqueous composition according to point 24, characterized in that the salt concentration in the composition excluding the biscationic compound and its one or more counter ions is between 25 mM and 100 mM.

26. The aqueous composition according to any of the points 14 to 25, characterized in that the biscationic compound is selected from the group consisting of a bis-benzimidazolium cation, a bis-imidazolium cation, and a bis-guanidinium cation.

27. A method for purifying a nucleic acid, characterized in that the method comprises the steps of
   a. providing the following components:
      (i) a solid phase capable of reversibly binding nucleic acids;
      (ii) an aqueous buffered solution containing the nucleic acid and a biscationic organic compound;
   b. contacting the provided components under conditions suitable for adsorbing the nucleic acid to the solid phase;
   c. separating the solid phase with the adsorbed nucleic acid from the solution;
   d. eluting the nucleic acid from the solid phase;
   thereby purifying the nucleic acid.

28. The method according to point 27, characterized in that the aqueous buffered solution of (ii) in step (a) contains one or more salts at a concentration below 500 mM.

29. The method according to point 28, characterized in that the salt concentration in the aqueous buffered solution is between 1 mM and 400 mM.

30. The method according to point 29, characterized in that the salt concentration in the aqueous buffered solution is between 5 mM and 300 mM.

31. The method according to point 30, characterized in that the salt concentration in the aqueous buffered solution is between 10 mM and 250 mM.

32. The method according to point 31, characterized in that the salt concentration in the aqueous buffered solution is between 20 mM and 150 mM.

33. The method according to point 32, characterized in that the salt concentration in the aqueous buffered solution is between 25 mM and 100 mM.

34. The method according to any of the points 27 to 33, characterized in that the aqueous buffered solution of (ii) in step (a) is a solution of compounds excluding a guanidinium salt.

35. The method according to any of the points 27 to 33, characterized in that the aqueous buffered solution of (ii) in step (a) is a solution of compounds excluding one or more compounds selected from the group consisting of sodium iodide, sodium perchlorate, guanidinium thiocyanate, guanidinium isothiocyanate, guanidinium hydrochloride, and urea.

36. The method according to any of the points 27 to 33, characterized in that the aqueous buffered solution of (ii) in step (a) is a solution of compounds excluding one or more chaotropic agents.

37. The method according to any of the points 27 to 36, characterized in that the composition is a solution of compounds excluding ethanol and isopropanol.

38. The method according to any of the points 27 to 36, characterized in that the composition is a solution of compounds excluding a C1-C5 aliphatic alcohol.

39. The method according to any of the points 27 to 38, characterized in that the nucleic acid is DNA or RNA.

40. The method according to any of the points 27 to 39, characterized in that the biscationic compound is selected from the group consisting of a bis-benzimidazolium cation, a bis-imidazolium cation, and a bis-guanidinium cation.

41. A kit of parts for isolating a nucleic acid, comprising a solid phase capable of reversibly binding nucleic acids and vial containing a buffered solution of a biscationic compound.

42. The kit according to point 41, characterized in that the solid phase is a silica fleece or magnetic particles coated with silica.

43. The kit according to any of the points 41 and 42, characterized in that the biscationic compound is selected from the group consisting of a bis-benzimidazolium cation, a bis-imidazolium cation, and a bis-guanidinium cation.

The examples and figures are provided to aid the understanding of the present invention, the true scope of which is set forth in the appended claims. It is understood that modifications can be made in the procedures set forth without departing from the spirit of the invention.

EXAMPLE 1

Adsorption of Nucleic Acids to Glass Fleece

The glass fleece was provided as the solid phase in commercially available HIGH PURE spin columns (from a kit of Roche Diagnostics GmbH, Applied Science, Cat. No. 11796828001; Roche Diagnostics GmbH Mannheim). The nucleic acid adsorbed to the glass fleece was Calf Thymus DNA (Roche Diagnostics GmbH, Applied Science, Id. No. 10041785 which is also part of different kits distributed by Roche Diagnostics GmbH, Germany). Apart from the adsorption solution all steps for nucleic acid purification were performed as recommended by the manufacturer.

The compositions of the adsorption solutions tested were as indicated in Table 1. An amount of 50 μg was dissolved in each adsorption solution, resulting in an aliquot with a volume of 500 μl. Each aliquot was applied to a spin column and the liquid was passed through the glass fleece at the bottom of the spin column by centrifugation.

Elution buffers and conditions were as given in the user manual provided with the kit (that is: elution was performed using an aliquot of 500 μl elution buffer, 10 mM tris-HCl buffer, pH 8.

The concentration of DNA in the adsorption solution was determined prior to the adsorption step using the PICOGREEN assay (Invitrogen, Cat. No. P7589). Furthermore, using the PICOGREEN assay, the residual DNA concentration in each adsorption buffer after being passed through the glass fleece (that is: after the adsorption step) was determined. Using these measurements, the relative amount of DNA bound to the solid phase was determined for each adsorption solution.

In addition, the DNA concentration in the eluate was determined, however using photometric determination at 260 nm.

TABLE 1

| Adsorption solution | DNA bound to solid phase | eluted DNA |
|---|---|---|
| MBITS, 50 mM; MES buffer, 50 mM pH 6.0 | 99.98% | 74.30% |
| BGDS, 37 mM MES buffer, 50 mM pH 6.0 | 99.40% | 62.40% |
| MITS, 50 mM MES buffer, 50 mM pH 6.0 | 100.00% | 58.20% |
| BITS, 50 mM | 99.94% | 59.46% |

TABLE 1-continued

| Adsorption solution | DNA bound to solid phase | eluted DNA |
|---|---|---|
| MES buffer, 50 mM pH 6.0 Control: Guanidinium thiocyanate, 1 M MES buffer, 50 mM pH 6.0 | 98.72% | 68.4% |

The results indicate that the biscationic compounds performed equally well as the conventional adsorption solution.

What is claimed is:

1. A method for binding a nucleic acid to a solid phase comprising the steps of
combining the solid phase and an aqueous solution comprising the nucleic acid, a biscationic organic compound, and a buffer salt, wherein the solution has a salt concentration exclusive of the biscationic organic compound between 5 and 300 mM under conditions suitable for binding of the nucleic acid to the solid phase.

2. The method of claim 1 wherein the biscationic compound is selected from the group consisting of a bis-benzimidazolium cation, a bis-imidazolium cation, and a bis-guanidinium cation.

3. An aqueous solution useful for adsorbing a nucleic acid to a solid phase, the solution comprising the nucleic acid, a biscationic organic compound, and a buffer salt, wherein the solution has a salt concentration exclusive of the biscationic organic compound between 5 and 300 mM, wherein the biscationic compound is selected from the group consisting of a bis-benzimidazolium cation, a bis-imidazolium cation, and guanidine, N,N'''-1,4-butanediyl cation.

4. A method for purifying a nucleic acid comprising the steps of
contacting a solid phase capable of reversibly binding the nucleic acid with an aqueous solution comprising the nucleic acid, a biscationic organic compound, and a buffer salt, wherein the solution has a salt concentration exclusive of the biscationic organic compound between 5 and 300 mM under conditions whereby the nucleic acid binds to the solid phase,
separating the solid phase with the bound nucleic acid from the solution, and
eluting the nucleic acid from the solid phase, thereby purifying the nucleic acid.

5. The method of claim 4 wherein the biscationic compound is selected from the group consisting of a bis-benzimidazolium cation, a bis-imidazolium cation, and a bis-guanidinium cation.

6. A kit of parts for isolating a nucleic acid, the kit comprising a solid phase capable of reversibly binding the nucleic acid and a reagent comprising a buffered solution of a biscationic compound selected from the group consisting of a bis-benzimidazolium cation, a bis-imidazolium cation, and guanidine, N,N'''-1,4-butanediyl cation.

7. The kit of claim 6 wherein the solid phase is selected from the group consisting of silica fleece and magnetic particles coated with silica.

* * * * *